US00PP34343P2

(12) United States Plant Patent
Capo

(10) Patent No.: US PP34,343 P2
(45) Date of Patent: Jun. 14, 2022

(54) ***PETUNIA* PLANT NAMED 'KLEPH22428**

(50) Latin Name: *Petunia hybrida*
Varietal Denomination: KLEPH22428

(71) Applicant: Klemm+Sohn GmbH & Co. KG, Stuttgart (DE)

(72) Inventor: Antonella Capo, Latina (IT)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 20 days.

(21) Appl. No.: 17/397,541

(22) Filed: Aug. 9, 2021

(51) Int. Cl.
*A01H 5/02* (2018.01)
*A01H 6/82* (2018.01)

(52) U.S. Cl.
USPC ..... Plt./356.12

(58) Field of Classification Search
USPC ..... Plt./263.1, 356, 356.21, 356.12
See application file for complete search history.

*Primary Examiner* — Karen M Redden
(74) *Attorney, Agent, or Firm* — Weatherly IP Solutions, LLC; James M. Weatherly

(57) ABSTRACT

A new *Petunia* plant named 'KLEPH22428' particularly distinguished by double, dark violet blue flowers, is disclosed.

1 Drawing Sheet

Genus and species: *Petunia hybrida.*
Variety denomination: 'KLEPH22428'.

BACKGROUND OF THE NEW PLANT

The present invention comprises a new and distinct variety of *Petunia*, botanically known as *Petunia hybrida* and hereinafter referred to by the variety name 'KLEPH22428'. 'KLEPH22428' is a selection from a cross-pollination of the commercial female *Petunia* line '*Petunia* Blue Ray' (patent status unknown) and the proprietary male *Petunia* line 'PH-2013-3926' (unpatented).

In July of 2015, the proprietary female *Petunia* line '*Petunia* Blue Ray' and the male *Petunia* line 'PH-2013-3926' were cross pollinated in Latina, Italy and seeds were obtained. The seeds were sown and plants were grown for evaluation. A plant line was selected in April 2016 in Latina, Italy and named 'KLEPH22428'. In May 2016, 'KLEPH22428' was first vegetatively propagated by terminal tip cuttings and tissue culture in Latina, Italy. 'KLEPH22428' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Double, dark violet blue flowers.

DESCRIPTION OF THE PHOTOGRAPH

This new *Petunia* plant is illustrated by the accompanying photograph, which shows a close-up of the flower of the plant. The plant is about 13 weeks old, grown indoors in Latina, Italy in March 2017. The colors shown are as true as can be reasonably obtained by conventional photographic procedures.

DESCRIPTION OF THE NEW VARIETY

The following detailed descriptions set forth the distinctive characteristics of 'KLEPH22428'. The data which define these characteristics were collected from asexual reproductions carried out in Latina, Italy. Data was collected on fourteen-week-old plants grown indoors in Latina, Italy under greenhouse conditions in May 2021. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH22428'.

Parentage:
- *Female.*—Commercial *Petunia* line '*Petunia* Blue Ray'.
- *Male.*—Proprietary *Petunia* line 'PH-2013-3926'.

Plant:
- *Form.*—Compact.
- *Habit.*—Semi-upright.
- *Height* (*from top of soil*).—13.0 cm.
- *Width* (*horizontal plant diameter*).—35.0 cm.
- *Propagation.*—Vegetative by terminal tip cuttings and tissue culture.
- *Time to produce a finished flowering plant.*—About 14 weeks in winter under short day conditions, about 8.5 weeks in spring.
- *Time to initiate and develop roots.*—2 to 3 weeks.
- *Root description.*—Moderate density, moderate branching, white roots.

Stems:
- *Average number* (*basal*).—7.
- *Length of basal branches* (*from the base of the stem to the tip*).—20.0 cm.
- *Internode length.*—0.5 cm.
- *Diameter of branches* (*from midpoint*).—0.35 cm.
- *Stem color.*—RHS 144A.
- *Anthocyanin.*—Absent.
- *Texture.*—Pubescent.

Leaves:
- *Arrangement.*—Alternate along the stem and opposite under the inflorescence.

*Length.*—4.7 cm.
*Width.*—3.5 cm.
*Shape.*—Elliptic.
*Apex.*—Acute.
*Base.*—Attenuate.
*Margin.*—Entire.
*Immature leaf color.*—Upper surface: RHS 138A. Lower surface: RHS 138B.
*Mature leaf color.*—Upper surface: RHS 137B. Lower surface: RHS 137D.
*Texture.*—Upper surface: Pubescent. Lower surface: Pubescent.
*Venation pattern.*—Arcuate.
*Venation color.*—Upper surface: RHS 137B. Lower surface: RHS 144C.
*Petioles.*—Length: 0.6 cm. Diameter: 0.5 cm. Color: RHS 144D. Texture: Pubescent.

Flower bud:
*Shape.*—Irregularly oblong.
*Length.*—2.5 cm.
*Diameter.*—1.0 cm.
*Color at tight bud.*—RHS 79A.
*Texture.*—Pubescent.

Inflorescence:
*Blooming habit (flowering season).*—Continuously flowering during spring and summertime.
*Inflorescence type.*—Sympodial, with monochasial growth.
*Number of flowers per node.*—1.
*Lastingness of individual blooms on the plant.*—About 10 days.
*Fragrance.*—Slight sweet smell.
*Flowers.*—Arrangement: Dense double flower composed of more than 30 petals. irregularly fused at the base. Diameter (flower face): 4.5 cm. Depth (total length of flower): 4.0 cm. Throat/Funnel: Not applicable for double flower. Petals: Color, mature flower (fully opened): Upper surface: RHS most similar color 86A. Lower surface: RHS 86D. Apex: Cuspidate. Base: Fused. Shape: Double. Margin: Entire. Strength of waviness: Not applicable. Degree of lobation: Not applicable.
*Calyx arrangement.*—Whorl of 5 sepals, fused at the base. Sepals: Color: Upper surface: RHS 137B. Lower surface: RHS 137B. Length: 1.8 cm. Width: 0.6 cm. Shape: Elliptic. Apex: Acute. Base: Attenuate. Margin: Entire. Texture: Upper surface: Pubescent. Lower surface: Pubescent.
*Pedicels.*—Color: RHS 144A. Length: 2.2 cm. Diameter: 0.3 cm. Texture: Pubescent.

Reproductive organs:
*Stamens.*—Quantity: Irregular number of supernumerary stamens mostly not normally developed and irregularly fused to petals. Shape: Needle with oblong head. Filament: Length: 0.9 cm. Diameter: 0.02 cm. Color: RHS 155C. Anther: Shape: Oblong (mostly not normally developed). Color: RHS 91A. Length: 0.15 cm. Diameter: 0.1 cm. Pollen: Absent. Pistils: Absent.

Fruit and seed set: None observed.
Disease and pest/insect resistance: None observed.

COMPARISON WITH PARENTAL LINES AND KNOWN VARIETY

'KLEPH22428' is a distinct variety of *Petunia*. 'KLEPH22428' is distinguished from its parents as described in Table 1 and Table 2:

TABLE 1

Comparison with Female Parental Line

| Characteristic | Variety 'KLEPH22428' | Female parent 'Petunia Blue Ray' |
|---|---|---|
| Flower type | Double | Single |

TABLE 2

Comparison with Male Parental Line

| Characteristic | Variety 'KLEPH22428' | Male Parent 'PH-2013-3926' |
|---|---|---|
| Flower color | Dark violet blue | Purple violet |

'KLEPH22428' is most similar to the commercial *Petunia* plant named 'KLEPH13235' (U.S. Plant Pat. No. 26,783). Differences between the two varieties are described in Table 3:

TABLE 3

Comparison with Similar Variety

| Characteristic | Variety 'KLEPH22428' | Commercial line 'KLEPH13235' |
|---|---|---|
| Flower color | Violet blue | Purple violet |

I claim:

1. A new and distinct variety of *Petunia* plant named 'KLEPH22428' as illustrated and described herein.

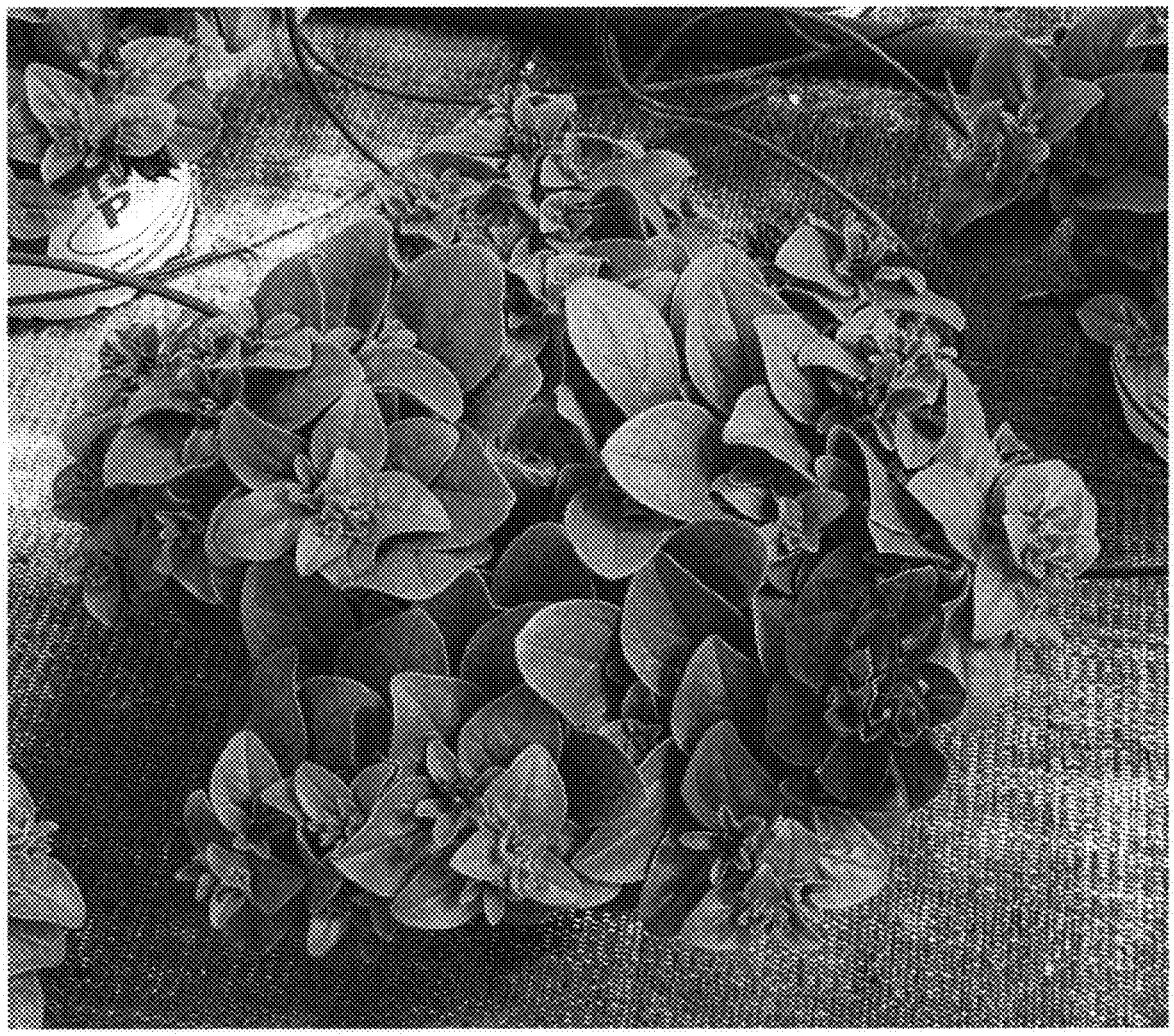

* * * * *